(12) United States Patent
Pugh et al.

(10) Patent No.: US 8,001,825 B2
(45) Date of Patent: Aug. 23, 2011

(54) AUTO-CALIBRATING METERING SYSTEM AND METHOD OF USE

(75) Inventors: Jerry T. Pugh, Santa Rosa, CA (US); Koon-wah Leong, Sunnyvale, CA (US); Arjuna Karunaratne, Fremont, CA (US)

(73) Assignee: LifeScan, Inc., Milpitas, CA (US)

( * ) Notice: Subject to any disclaimer, the term of this patent is extended or adjusted under 35 U.S.C. 154(b) by 598 days.

(21) Appl. No.: 11/947,964

(22) Filed: Nov. 30, 2007

(65) Prior Publication Data

US 2009/0139300 A1 Jun. 4, 2009

(51) Int. Cl.
*G01N 31/22* (2006.01)
*G01D 11/24* (2006.01)

(52) U.S. Cl. ............ 73/1.02; 73/1.01; 422/87; 422/403; 422/404

(58) Field of Classification Search ............... 73/1.01, 73/1.02, 431; 221/260–272; 422/58, 61, 422/50, 55, 87, 400, 401, 403, 404; 600/365, 600/309, 316, 345, 347; 205/792
See application file for complete search history.

(56) References Cited

U.S. PATENT DOCUMENTS

| | | | |
|---|---|---|---|
| 4,088,448 A | 5/1978 | Lilja et al. | |
| 4,142,863 A | 3/1979 | Covington et al. | |
| 4,476,149 A | 10/1984 | Poppe et al. | |
| 4,554,064 A | 11/1985 | McClintock et al. | |
| 4,578,716 A | 3/1986 | van Rijckevorsel et al. | |
| 4,852,025 A | 7/1989 | Herpichbohm et al. | |
| 5,053,199 A | 10/1991 | Keiser et al. | |
| 5,108,564 A | 4/1992 | Szuminsky et al. | |
| 5,171,689 A | 12/1992 | Kawaguri et al. | |
| 5,312,590 A | 5/1994 | Gunasingham | |
| 5,325,853 A * | 7/1994 | Morris et al. ............ | 204/403.02 |
| 5,366,609 A | 11/1994 | White et al. | |
| 5,395,504 A | 3/1995 | Saurer et al. | |
| 5,399,256 A | 3/1995 | Bohs et al. | |
| 5,505,308 A | 4/1996 | Eikmeier et al. | |
| 5,525,297 A | 6/1996 | Dinger et al. | |
| 5,609,823 A | 3/1997 | Harttig et al. | |
| 5,628,890 A | 5/1997 | Carter et al. | |
| 5,679,311 A | 10/1997 | Harttig et al. | |
| 5,797,693 A | 8/1998 | Jaeger et al. | |
| 5,856,195 A | 1/1999 | Charlton et al. | |

(Continued)

FOREIGN PATENT DOCUMENTS

AU 5487394 A 8/1994

(Continued)

OTHER PUBLICATIONS

European Search Report No. EP 03 00 7604 dated May 19, 2003.

(Continued)

*Primary Examiner* — David A. Rogers
(74) *Attorney, Agent, or Firm* — Nutter McClennen & Fish LLP

(57) ABSTRACT

Methods of auto-calibrating a meter are disclosed. In one aspect, the method can include determining a set of calibration information applicable to a sensor and storing the calibration information onto a tag element associated with a sensor dispenser. The tag element can be placed into communication with a reader element that is associated with a meter and which is configured to receive the calibration information so as to allow the meter to use the calibration information in a calibration procedure. Various aspects of a system for auto-calibrating a meter are also disclosed.

23 Claims, 9 Drawing Sheets

U.S. PATENT DOCUMENTS

| | | | |
|---|---|---|---|
| 5,880,829 | A | 3/1999 | Kauhaniemi et al. |
| 5,904,898 | A | 5/1999 | Markart |
| 5,942,102 | A | 8/1999 | Hodges et al. |
| 5,989,917 | A | 11/1999 | McAleer et al. |
| 6,027,689 | A | 2/2000 | Markart et al. |
| 6,176,119 | B1 | 1/2001 | Kintzig et al. |
| 6,180,063 | B1 | 1/2001 | Markart et al. |
| 6,193,873 | B1 | 2/2001 | Ohara et al. |
| 6,251,260 | B1 | 6/2001 | Heller et al. |
| 6,284,125 | B1 | 9/2001 | Hodges et al. |
| 6,299,757 | B1 | 10/2001 | Feldman et al. |
| 6,378,702 | B1 | 4/2002 | Kintzig et al. |
| 6,413,410 | B1 | 7/2002 | Hodges et al. |
| 6,475,372 | B1 | 11/2002 | Ohara et al. |
| 6,676,995 | B2 | 1/2004 | Dick et al. |
| 6,689,411 | B2 | 2/2004 | Dick et al. |
| 6,716,577 | B1 | 4/2004 | Yu et al. |
| 6,749,887 | B1 | 6/2004 | Dick et al. |
| 6,780,645 | B2 | 8/2004 | Hayter et al. |
| 6,827,899 | B2 | 12/2004 | Maisey et al. |
| 6,830,934 | B1 | 12/2004 | Harding et al. |
| 6,952,950 | B2* | 10/2005 | Doe et al. .................. 73/54.01 |
| 6,997,343 | B2 | 2/2006 | May et al. |
| 7,063,234 | B2 | 6/2006 | Giraud et al. |
| 7,178,416 | B2* | 2/2007 | Whelan et al. ............ 73/864.91 |
| 7,449,148 | B2 | 11/2008 | Matsumoto et al. |
| 7,582,262 | B2* | 9/2009 | Funke et al. ................... 422/99 |
| 7,628,292 | B2* | 12/2009 | Lancesseur et al. ......... 221/267 |
| 2002/0057993 | A1 | 5/2002 | Maisey et al. |
| 2002/0104849 | A1* | 8/2002 | Giruad ........................ 221/270 |
| 2002/0150501 | A1 | 10/2002 | Robertson et al. |
| 2003/0032190 | A1 | 2/2003 | Brown et al. |
| 2003/0089730 | A1 | 5/2003 | May et al. |
| 2003/0116583 | A1 | 6/2003 | Pugh |
| 2003/0175155 | A1* | 9/2003 | Charlton ....................... 422/61 |
| 2003/0185708 | A1* | 10/2003 | Otake ............................ 422/61 |
| 2003/0186446 | A1 | 10/2003 | Pugh |
| 2003/0223906 | A1* | 12/2003 | McAllister et al. ............ 422/58 |
| 2004/0007585 | A1 | 1/2004 | Griffith et al. |
| 2004/0050717 | A1 | 3/2004 | Teodorczyk et al. |
| 2004/0178216 | A1 | 9/2004 | Brickwood et al. |
| 2005/0118071 | A1* | 6/2005 | Sacherer ...................... 422/100 |
| 2005/0186162 | A1 | 8/2005 | Sato |
| 2005/0240369 | A1* | 10/2005 | Diorio et al. ................. 702/107 |
| 2005/0240370 | A1* | 10/2005 | Diorio et al. ................. 702/107 |
| 2005/0281706 | A1* | 12/2005 | Funke et al. .................... 422/63 |
| 2006/0104861 | A1 | 5/2006 | Windus-Smith et al. |
| 2006/0226985 | A1* | 10/2006 | Goodnow et al. .......... 340/572.1 |
| 2007/0034630 | A1* | 2/2007 | Lancesseur et al. .......... 220/281 |
| 2007/0172388 | A1* | 7/2007 | Padmanabhan et al. ........ 422/58 |
| 2007/0208308 | A1* | 9/2007 | Gibson et al. ................ 604/131 |
| 2007/0233395 | A1* | 10/2007 | Neel et al. ...................... 702/19 |
| 2008/0068197 | A1* | 3/2008 | Neubauer et al. .......... 340/686.1 |
| 2008/0114228 | A1* | 5/2008 | McCluskey et al. .......... 600/365 |
| 2008/0164280 | A1 | 7/2008 | Kuriger et al. |
| 2008/0208042 | A1* | 8/2008 | Ortenzi et al. ................ 600/432 |
| 2009/0159444 | A1* | 6/2009 | Ghesquiere et al. ..... 204/403.02 |
| 2009/0178937 | A1* | 7/2009 | Taylor ........................... 205/792 |

FOREIGN PATENT DOCUMENTS

| | | |
|---|---|---|
| DE | 3103484 | 8/1982 |
| DE | 3708031 | 11/1987 |
| EP | 0290770 A2 | 11/1988 |
| EP | 0400918 | 12/1990 |
| EP | 0609760 A1 | 8/1994 |
| EP | 0735363 A1 | 10/1996 |
| EP | 0-928967 A2 | 7/1999 |
| EP | 1-081490 A1 | 3/2001 |
| JP | 3167464 A | 7/1991 |
| JP | 0434306 | 11/1992 |
| JP | 04343065 A | 11/1992 |
| JP | 5002007 A | 1/1993 |
| JP | 6222874 | 8/1994 |
| SU | 1351627A A2 | 11/1987 |
| WO | 94/19684 A1 | 9/1994 |
| WO | 9429731 A1 | 12/1994 |
| WO | 99/32881 A1 | 7/1999 |
| WO | 99/60391 A1 | 11/1999 |
| WO | 02/26129 A1 | 4/2002 |
| WO | 03/085392 A1 | 10/2003 |

OTHER PUBLICATIONS

Osamu, Niwa, et al. "Electrochemical Behavior of Reversible Redox Species at Interdigitated Array Electrodes with Different Geometries: Consideration of Redox Cycling and Collection Efficiency", Analytical Chemistry; Mar. 1990, vol. 62, No. 5, pp. 447-452.

* cited by examiner

AUTO-CALIBRATING METERING SYSTEM AND METHOD OF USE

FIELD OF USE

The present disclosure relates to systems and methods of calibrating a meter for use with a particular sensor, in particular to systems and methods of auto-calibrating a meter.

BACKGROUND

Analyte detection in physiological fluids, e.g. blood or blood-derived products, is of ever increasing importance to today's society. Analyte detection assays find use in a variety of applications, including clinical laboratory and home testing where the results can play a prominent role in diagnosis and management of various disease conditions. Analytes of interest can include glucose for diabetes management, cholesterol, and the like. In response to this growing importance of analyte detection, a variety of analyte detection protocols and devices for both clinical and home use have been developed.

One common type of system that allows people to conveniently monitor their blood glucose levels includes a sensor (e.g., a disposable test strip) configured to receive a blood sample, and a meter that "reads" the test strip to determine the associated blood-glucose level. The test strip typically includes one end having an electrical contact area for mating with the meter and a second end containing any necessary reagents (e.g., glucose oxidase and a mediator) and electrodes. To initiate testing, the sensor is inserted into the meter and a blood sample is applied to the sample chamber. The meter then applies a voltage to the electrodes thereby causing a redox reaction. Next, the meter measures the resulting charge and/or current and calculates the glucose level based on the reading. After the test, the test strip can be disposed of and new strips can be used for additional testing.

In use, it is often necessary to calibrate the meter with respect to each sensor prior to each use. For example, the sensors to be used may have been produced from different production lots or batches thereby resulting in some manufacturing variability. Also, different types of sensors (e.g., testing for different analytes) can be used with the same meter thereby requiring the meter to recognize the sensor before use. In short, it may be crucial to the accuracy of a test to transfer some information between the meter and the sensor.

Currently, the user is typically required to identify any necessary calibration information (e.g., a calibration code may be printed on a label for a sensor or container of sensors) and further required to manually input the information into the meter. However, calibrating the meter each time a new sensor (or cartridge of sensors) is utilized, or indeed each time the user wishes to perform a test, can be inconvenient, and potentially life-threatening, due to the number of steps involved and the time consuming nature of the process. It is also inconvenient for the user to perform this calibration step, particularly if the required calibration information is printed on the sensor packaging that potentially could have been discarded or if the user is in a hurry, for example, experiencing a period of hypoglycemia, in which case their thought processes could be blurred. Additionally, looking for small print on a label can be problematic for many diabetics, too, as diminished eyesight is often a resultant complication of the disease. Many users may also forget to enter the calibration information or they may decide not to enter the information if they do not understand its significance thereby resulting in an unreliable test and potentially harmful results.

Thus, there remains a need for an easy to use measuring system configured to provide accurate and reliable results.

SUMMARY

A method and system of allowing for auto-calibration of a metering device is provided herein. In general, the various embodiments described below allow for a meter to receive and utilize various types and amounts of sensor-specific information (e.g., a calibration code) as the meter comes into communication with a corresponding sensor. More specifically, a plurality of sensors (or a single sensor) can be disposed within a sensor dispenser which is configured to deliver sensors to a meter to perform some desired test. As described herein, the sensor dispenser and the meter can be configured to communicate with one another such that sensor-specific information can be communicated between the sensor dispenser and the meter as the meter retrieves a sensor from the dispenser. In some embodiments, the information can be the same for all sensors packaged in the same sensor dispenser (e.g., all the sensors are from the same lot or share some other characteristic). In other embodiments, the meter can receive information from the sensor dispenser which allows the meter to distinguish between distinct sensors packaged in the same dispenser (e.g., a first calibration code should be used for the first 5 sensors received from the dispenser and a second calibration code should be used for the next five sensors received from the dispenser). As described below, the meter can use this information in various manners in order to provide accurate and reliable testing results. For example, the information can include a sensor-specific calibration code which can be incorporated into an internal calibration algorithm of the meter thereby preparing the meter for use.

Various embodiments of a method of auto-calibration of a meter are provided herein. In one such aspect, the method includes disposing a plurality (or at least one) of sensors within a sensor dispenser configured to deliver one sensor of the plurality to a meter upon demand. Next, the method can include determining a set of calibration information applicable to each sensor. Further, the method can include storing the calibration information onto a tag element and associating the tag element with the sensor dispenser. Next, the method can include placing the tag element into communication with a reader element associated with the meter wherein the reader element is configured to receive the information from the tag element. Also, the meter can be configured to perform a calibration procedure which is at least partially dependent upon the information. Further, the method can include activating either the tag or receiver element so as to allow the elements to communicate with one another.

As will be described below, the tag element and the reader element can be configured to communicate with one another in any of a wide variety of manners. For example, the elements can communicate with one another by various wireless and non-wireless technologies. For example, the tag element can be a radiofrequency ("RF") tag element and the reader element can be an RF reader element thereby utilizing RF technology to pass information between the elements.

The method can allow for the transfer of various types and amounts of sensor-specific information. For example, the information can include a calibration code(s) specific for those sensors disposed within the sensor dispenser, manufacture and/or expiry date of the various sensors, etc. In determining this information, a sub-set of sensors can be identified as a representative set of the plurality of sensors. Next, the sensors of the sub-set can be individually tested, and this information written onto a tag element.

Those skilled in the art will appreciate that various embodiments of the sensor dispenser and/or meter are within the spirit and scope of the present disclosure. For example, in an exemplary embodiment, the sensor dispenser can be substantially cylindrical with the tag element coupled to a distal end of the dispenser which can be configured to releasably engage the meter such that the reader element is in communication with the tag element when the meter is engaged to the sensor dispenser Those skilled in the art will also appreciate that any of a variety of meters capable of performing any of a variety of tests are within the spirit and scope of the presently disclosed embodiments. For example, in one embodiment, the meter is configured to determine an analyte (e.g., glucose) concentration of a sample (e.g., blood).

In another aspect, a method for measuring an analyte concentration in a blood sample is provided which includes providing a sensor dispenser having a plurality of sensors disposed therein. Similar to above, the sensor dispenser can be associated with some type of tag element configured to store a set of calibration information relating to the sensors disposed therein. Next, the method can include positioning a meter into communication with the sensor dispenser such that a reader element associated with the meter can receive (or transmit) information from the tag element (or from the meter to the tag element) during such coupling. The meter can use this information to perform any of a number of functions. For example, in an exemplary embodiment, the meter can utilize the information to perform an auto-calibration step which is at least partially dependent upon the information. Next, the method can include transferring a sensor from the sensor dispenser to the meter. Next, the method can also include applying a biological sample to the sensor and performing a desired analysis of the sample.

Additionally, various aspects of a system for auto-calibration of a meter are provided herein. In one such aspect, the system includes a sensor dispenser configured to retain at least one sensor(s). Similar to those embodiments mentioned above, the sensor dispenser can be associated with a tag element configured to store a set of information relating to the sensor(s) retained within the sensor dispenser. Next, the system can include a meter configured to receive a sensor from the sensor dispenser. Additionally, the meter can be associated with a receiver element configured to communicate with the tag element as the reader element is brought into communication with the tag element thereby allowing the meter to perform an auto-calibration step which is at least partially dependent upon the information received from the tag element. In other embodiments, the meter can also includes a counter element configured to determine a number of sensors received from a particular sensor dispenser thereby indicating to the user when the sensor dispenser is empty.

In other aspects, a system for auto-calibration of a meter is provided which includes a sensor dispenser configured to house at least one sensor. Additionally, the system includes a tag element associated with the sensor dispenser wherein the tag element can be configured to store a set of information relating to the sensor(s) housed within the sensor dispenser. The tag element can be further configured to communicate the information to a meter.

In yet another aspect, a system for auto-calibration of a meter is provided which includes a meter configured to receive a sensor from a sensor dispenser. The system can also include a reader element associated with the meter wherein the reader element can be configured to receive an amount of sensor-specific information from the sensor dispenser.

These aspects, and others, will be described in detail below.

BRIEF DESCRIPTION OF THE DRAWINGS

The presently disclosed embodiments will be more fully understood from the following detailed description taken in conjunction with the accompanying drawings, in which:

FIG. 11 is a perspective view of an exemplary embodiment of a meter configured for use with an embodiment of the sensor dispenser;

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the systems and methods described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Methods and systems for auto-calibration of a metering device are provided herein. More specifically, the methods and systems allow for at least one sensor to be disposed within a sensor dispenser. Next, some type of sensor-specific information can be determined and stored on a tag element which can then be associated (e.g., coupled or engaged) with the sensor dispenser. As will be described, the tag element can also be configured to communicate the information to a meter as the meter is brought into communication with the sensor dispenser (e.g., as the meter receives a sensor from the sensor dispenser). In some embodiments, a plurality of sensors can be disposed in the sensor dispenser wherein each of the sensors shares the same calibration information. In other embodiments, distinct sensors can be stored in a single sensor dispenser wherein the tag element can inform the meter of different information for the different sensors. For example, the tag element can be configured to inform the meter that a first plurality of sensors utilizes a first calibration information while a second plurality of sensors utilizes a second calibration information. In other embodiments, the meter can be configured to keep a count of how many sensors have been retrieved from a sensor dispenser thereby indicating to a user when the sensor dispenser is empty. Once the information is communicated to the meter (e.g., via wireless technology), the meter can use the sensor-specific information to perform any type of internal calibration step. For example, the information can be a calibration code which is utilized by an internal algorithm of the meter. Thus, the presently disclosed embodiments enable sensor-specific auto-calibration of the meter thereby eliminating any potential user error.

Figure 1:
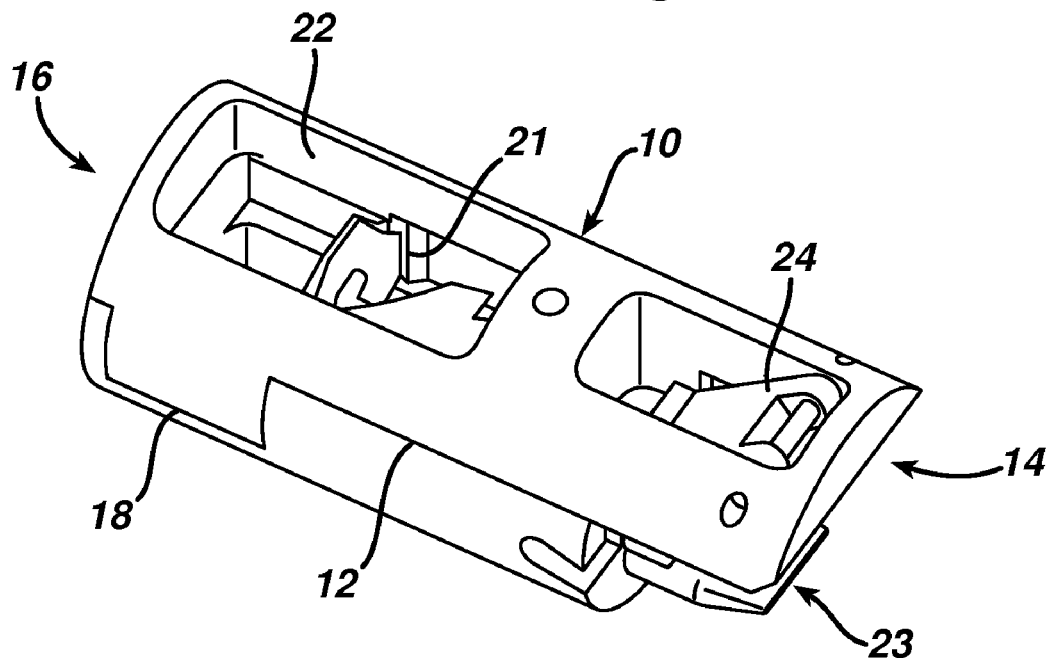
FIG. 1 is a perspective view of an exemplary embodiment of a sensor dispenser.

Those skilled in the art will appreciate that various such sensor dispensers are within the spirit and scope of the present disclosure. For example, FIG. 1 shows an exemplary embodiment of such a dispenser 10 which includes an elongate body 12 having a proximal end 14 and a distal end 16. The distal end of the elongate body 12 can include a storage area 18 for holding an array of connected sensors 20. In one embodiment, a series of folded sensors can be positioned within a cavity 22 and then individually dispensed from a proximally positioned feeder mechanism 24. One skilled in the art will appreciate that the location of the feeder mechanism 24 will depend on the orientation and configuration of the sensor dispenser 10 and could be positioned in any location adjacent to the storage chamber which would allow dispensing of the sensors (e.g., on top of, distally to, etc.).

Figure 2A:
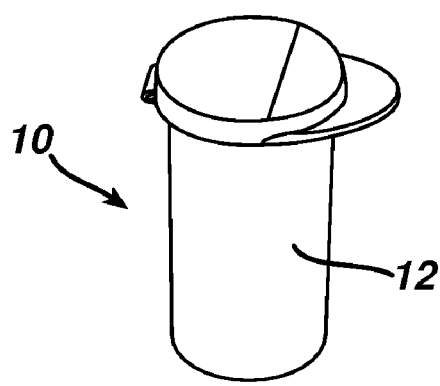
FIG. 2A is a perspective view of the sensor dispenser having a resealable opening.
Figure 2B:
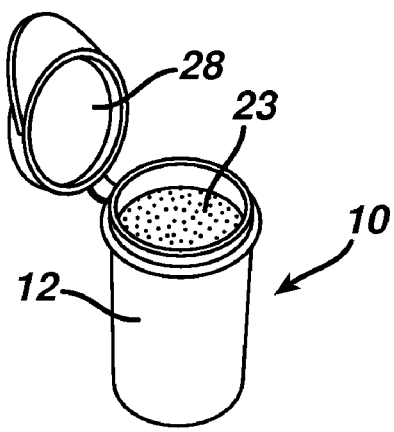
FIG. 2B is a perspective view of the sensor dispenser of FIG. 2A being opened at one end.

The body 12 of the dispenser 10 can have a variety of shapes including, for example, a generally cylindrical shape as shown in the FIGS. 1, 2A, and 2B. One skilled in the art will appreciate that a variety of alternative shapes capable of defining various configurations of a storage area 18 and feeder mechanism 24 are also within the spirit and scope of the present disclosure. The body 12 can also include features configured to protect sensors positioned within sensor dispenser 10. For example, the body 12 can enclose the storage area 18 and the feeder mechanism 24 in a protective shell, as shown in FIGS. 2A and 2B, thereby shielding the sensors 20 positioned therein from the environment. As shown, the body 12 can define a resealable chamber that limits exposure of sensors 20 to the atmosphere. When a user wishes to dispense a sensor, the body 12 can be opened via a resealable flap 28 to expose a proximally positioned dispensing surface 23. After dispensing a sensor, the flap 28 can be resealed to provide a generally airtight container. One skilled in the art will appreciate that dispenser 10 can include various alternative or additional openings having any of a variety of configurations capable of providing alternative mechanisms for accessing the feeder mechanism 24. Such resealable opening can include, for example, threaded openings, snap fit openings, frictional fit openings, tongue and groove openings, and combinations thereof.

The body 12 can be formed as a single piece with the cavity 22 and feeding mechanism 24 formed integrally, or can be formed from various connectable components. Additionally, the body can be configured to receive a second plurality of sensors following use of the first set of sensors, or the body 12 can be disposable following use of the first plurality of sensors. When the body 12 is configured to receive a second plurality of sensors, the storage area 18 can be detached from the dispenser 10 and a second storage area 18 (containing a new set of sensors) can be attached to sensor dispenser 10 thereby refilling the sensor dispenser. One skilled in the art will appreciate that storage area 18 can be mated with the sensor dispenser 10 in a variety of ways, such as, for example, with a snap fit, threads, slot and grove, or a combination thereof.

The body 12 can also be configured to enable visual inspection of the sensors disposed therein. For example, the elongate body 12 can include a window that allows a user to visually estimate the number of sensors remaining in the cavity 22 thereby allowing for a visual inspection to indicate when the current supply of sensors is running low. In other embodiments, the dispenser can include any of a variety of counting mechanisms, including electrical and mechanical based counters, configured to alert a user to the quantity of sensors remaining within the cavity 22.

Figure 3:
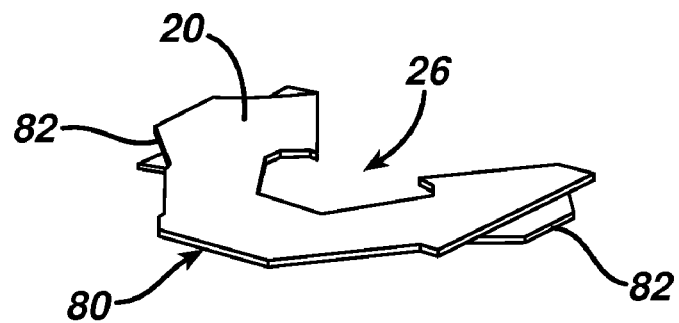
FIG. 3 is a perspective view of an exemplary embodiment of a sensor for use with the sensor dispenser.
Figure 4:
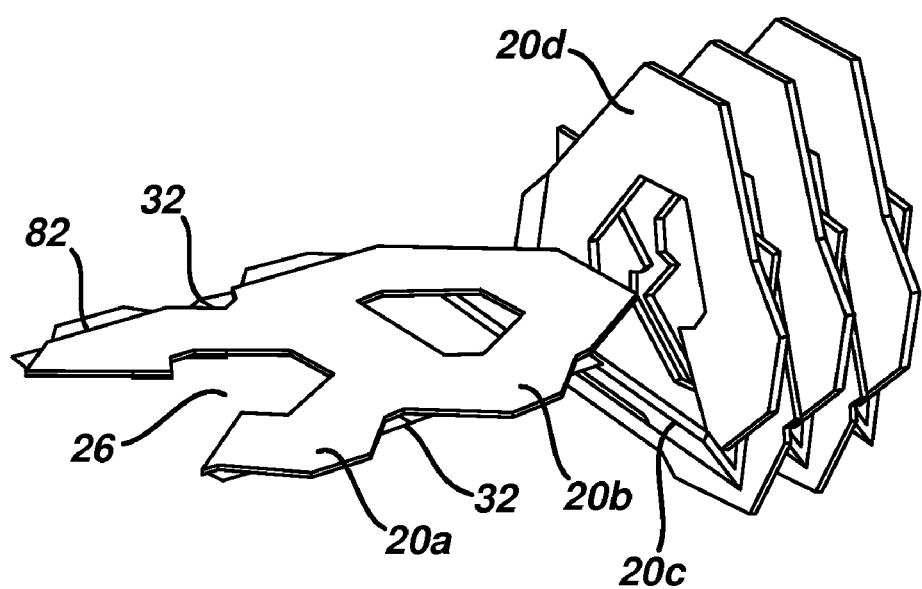
FIG. 4 illustrates an array of the sensors of FIG. 3 connected via flexible hinges.
Figure 5:
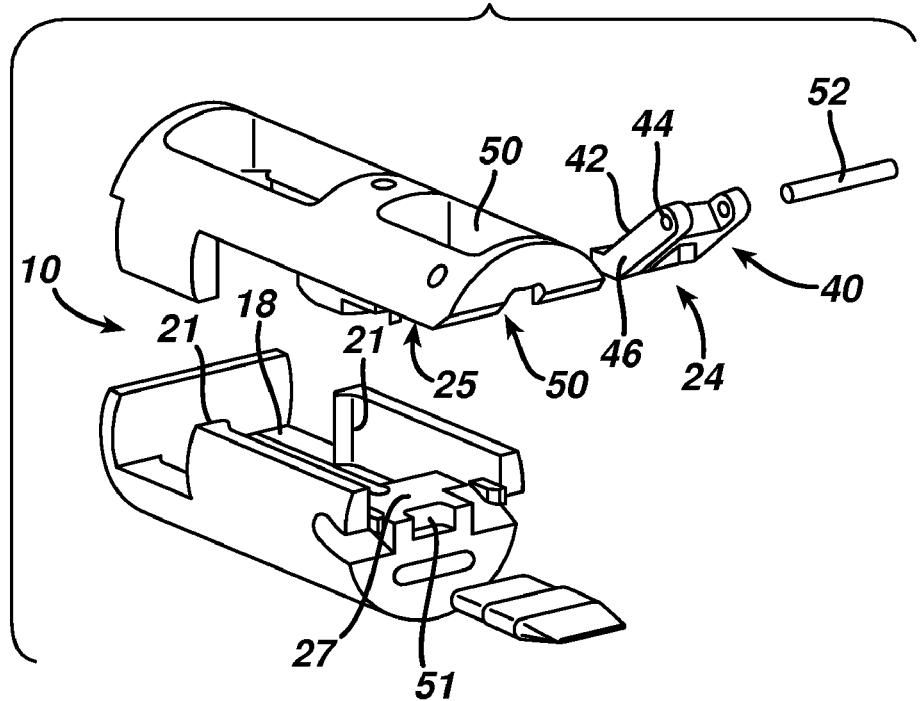
FIG. 5 is an exploded view of the sensor dispenser of FIG. 1.

The interior of the storage area 18 can have any of a variety of shapes configured to allow for the storage and delivery of various configurations of sensors 20. For example, the interior of the cavity 22 can be shaped to hold a folded array of sensors 20. As shown in FIGS. 3 and 4, such an array of sensors 20a, 20b, 20c, 20d etc. can be connected via flexible hinges 32. In such an embodiment, the sensors 20 can be folded at such hinges 32 for storage in a folded stack and then unfolded for dispensing. At least a portion of the storage area 18 can have a shape corresponding to the folded sensors. Additionally, the interior walls of the cavity 22 can include guide features 21 to assist with moving sensors 20 from the cavity 22 to the feeder mechanism 24. In one embodiment, the storage area 18 can include various guide features 21 configured to hold and/or to direct sensors 20 prior to delivery to the feeder mechanism 24. FIG. 5 illustrates an embodiment of such guide features 21. As shown, the guide features 21 can be defined by first and second protrusions that extend from the interior walls of the storage area 18 and serve to contain the folded stack of sensors. As the sensors 20 are pulled during a dispensing step, the first sensor in the stack of folded sensors can be pulled past the protrusions. In one aspect, the protrusions are sized such that the sensors 20 slightly flex (i.e., bend) as they are pulled past the protrusions. The guide features 21 can thus keep the folded stack of sensors orderly and can provide an open area between the folded stack of sensors and the feeder mechanism 24. This open area can allow sensors 20 to move into position for receipt by the feeding mechanism 24 and can also help to prevent jamming.

Figure 7:
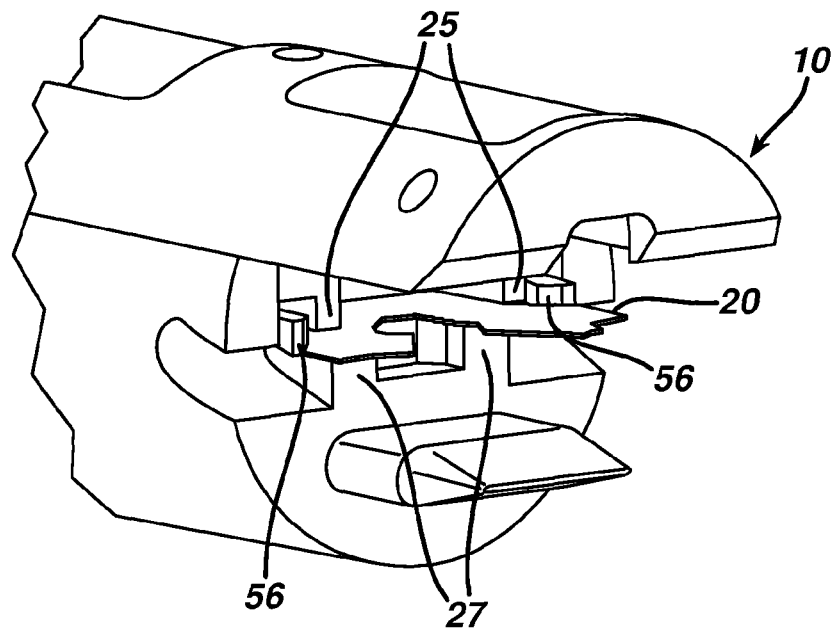
FIG. 7 illustrates the sensor dispenser of FIG. 6 in a dispensing configuration.

The feeding mechanism 24 can engage and hold the first sensor of the array in position until a meter activates the feeding mechanism (described below) thereby dispensing the first sensor to the meter. The feeding mechanism 24 can substantially limit or prevent any proximal and/or distal movement of the sensor in various manners. For example, FIG. 5 illustrates an exploded view of the sensor dispenser 10 of FIG. 1 thereby illustrating the feeder mechanism 24 with a sensor engaging member 40 configured to be movable between a biased sensor engaging position and a sensor dispensing position. For example, when a meter engages the dispenser 10, the sensor engaging member 40 is forced, by the meter, from the sensor engaging position to the sensor dispensing position thereby releasing the sensor from the feeder mechanism 24 and delivering the sensor to the meter. For example, FIG. 7 illustrates a sensor-engaging member 40 in a dispensing position.

Figure 6:
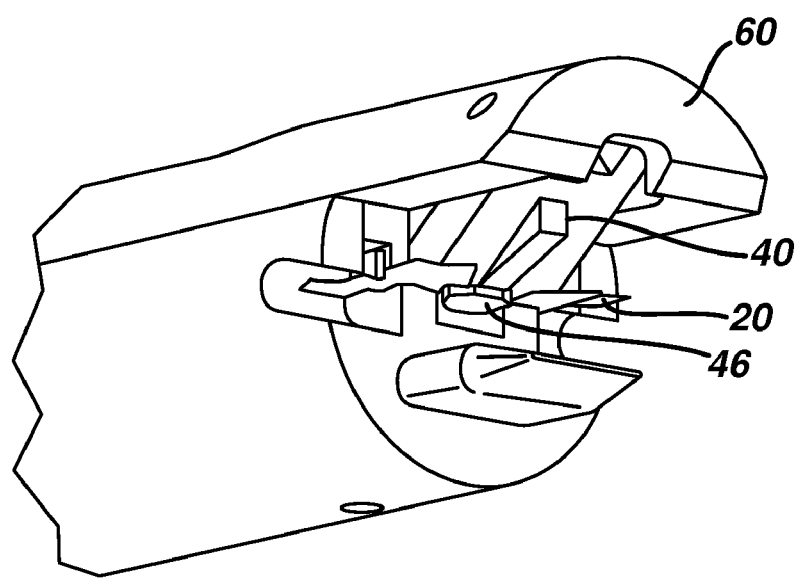
FIG. 6 is a partial perspective view of the dispensing end of the sensor dispenser of FIG. 1.

Various embodiments of a sensor engaging member 40 are included within the spirit and scope of the present disclosure. In an exemplary embodiment, the sensor engaging member 40 can include an elongate body 42 with a first end 44 mated with the body 12 and a second end 46 configured for mating with sensor 20. In those embodiments where a plurality of connected sensors are disposed within the sensor dispenser 10, the first sensor in the plurality can be held (i.e., retained within the sensor) by the sensor engaging member 40. For example, FIG. 6 shows the sensor-engaging member 40 in a sensor engaging position with a second end 46 of the engaging member 40 mated with the sensor 20. In this position, the sensor 20 cannot be dispensed.

Figure 8A:
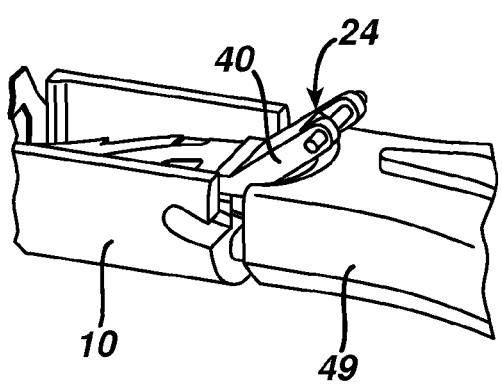
FIG. 8A is a cut-away view of the sensor dispenser partially engaged by a meter.
Figure 8B:
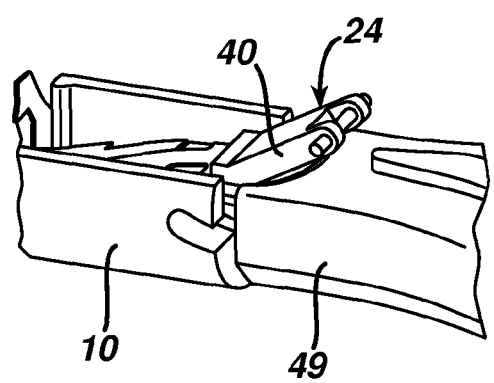
FIG. 8B is a cut-away view of the sensor dispenser of FIG. 8A with the sensor dispenser and meter being fully engaged.

As indicated above, coupling the sensor dispenser 10 with a meter FIGS. 8A and 8B illustrate a cut-away view of an embodiment of the sensor dispenser 10 engaged with a meter 49. In this example, as the meter 49 engages the proximal end of sensor dispenser 10 (feeder mechanism 24), the sensor-engaging member 40 can be lifted from the sensor engaging position by the force of meter 49 (FIG. 8B). The meter 49 can then mate with sensor 20.

As will be apparent to those skilled in the art, the sensor engaging member 40 can be mated to the dispenser 10 in various manners. For example, the sensor engaging member 40 can be pivotally fixed to the dispenser 10 such that the sensor-engaging member can pivot between a sensor engaging position and a sensor dispensing position. In one embodiment (as shown in FIG. 5), a pivot pin 52 can pivotally fix the engaging member 40 to the body 12. One skilled in the art will also appreciate that the sensor engaging member 40 can be mated with the body 12 in a variety of other manners that allow the sensor engaging member to move between a sensor engaging and a sensor dispensing position. In another exemplary embodiment, the sensor-engaging member 40 is fixedly mated to the body 12 and is flexible. In such an embodiment, when a meter engages feeder mechanism 24, the meter bends the sensor engagement member 40 and moves it from a sensor engaging position to a sensor dispensing position.

In one embodiment, the engaging member 40 is biased in the sensor engaging position. In use, the meter can be configured to move the sensor-engaging member 40 from a sensor engaging position to a sensor dispensing position. Further, as the meter is decoupled from the sensor dispenser, the engaging member 40 can return to the sensor engaging position. As will appreciated by those skilled in the art, the meter can be biased as such in various manners. For example, a spring can be positioned between the body 12 and the engaging member 40 in order to apply a downward force. Thus, the spring can allow the engaging member 40 to move upwards when coupled to the meter. Likewise, as the meter is removed (decoupled), the action of the spring can return the engaging member to the sensor engaging position. In an alternative embodiment, the engaging member can be formed of a resilient material. For example, the engaging member 40 can be fixedly mated with the body 12 in the sensor engaging position. When the meter contacts the engaging member 40, the engaging member 40 can be bent upwards to allow for dispensing. Likewise, when the meter is removed, the resilient engaging member 40 can return to its original position. Other exemplary means for biasing the engaging member include, for example, magnets and electromechanical actuators.

The sensor dispenser 10 can also include various other features to assist with dispensing a sensor(s) 20. For example, a proximal surface of the dispenser 10 can include stops 56 which prevent the sensor 20 from retreating into the dispenser 10. In use, the stops 56 can be configured to allow a sensor 20 to move in a proximal (dispensing) direction but limit (or prevent) distal movement. Thus, as the sensor 20 moves into position in the feeding mechanism 24, the stops 56 can be positioned and configured to contact the sides of the sensor 20. In one embodiment, as shown in FIG. 7, the stops 56 can have a taper that corresponds to a "V" shape of the sensor 20. When the sensor 20 moves past the stops 56, the stops 56 can contact the sides of the sensor 20 thereby limiting or preventing distal movement. One skilled in the art will appreciate that the configuration of the stops 56 can be adapted to the shape of the sensor 20.

The stops 56 can also be configured to cooperate with the engaging member 40 in order to control movement of the sensor(s) 20. For example, when a sensor 20 is engaged within the feeder mechanism 24, the stops 56 can limit or prevent distal movement of the sensor 20 while the engaging member 40 can limit or prevent proximal movement. Thus, taken together, the stops 56 and the engaging member 40 can be configured to control the movement of the sensor 20. In an alternative embodiment, the engaging member 40 can be configured to mate with the sensor 20 such that it limits or prevents both proximal and distal movement.

The dispenser 10 can also include various other features configured to assist with effectively and efficiently dispensing a sensor(s) 20. For example, proximally positioned top and bottom interior surfaces 25 and 27 of the body 12, respectively, can assist with directing the sensors into communication with the engaging mechanism 40. As shown in FIG. 5, the surfaces 25 and 27 are generally flat and spaced apart by a distance of less than the height of a storage chamber 18. As the connected sensors are pulled from the storage chamber, the sensors 20 can encounter the surfaces 25 and 27 and are thereby directed into contact with the engagement member 40. In one aspect, the top and/or bottom surfaces 25, 27 are sloped to help direct the sensor(s) 20. For example, the top surface 25 can slope downward and/or the bottom surface 27 can slope upward thereby acting to funnel the sensor(s) 20 into the feeding mechanism 24. Additionally, the top surface 25 can also include a recess or opening 50 configured to receive the sensor-engaging mechanism 40 as the sensor engaging mechanism moves into a sensor dispensing position (as shown in FIG. 5). In use, the recess 50 can be configured to allow the sensor dispensing mechanism 40 to move out of the way of (e.g., disengage) a sensor 20 during the dispensing procedure. In other embodiments, a second recessed area 51 can be positioned in the bottom interior surface 27 for receiving at least a portion of the engaging mechanism 40, for example, the engaging member 40 can be seated within the recess 51 while member 40 is in the sensor engaging position.

The dispenser 10 can also include various alignment features capable of facilitating the alignment and coupling of the feeder mechanism 24 with a meter 49. In particular, the alignment features can help bring meter 49 into communication (e.g., contact) with the feeder mechanism 24 thereby activating the feeder mechanism 24 which delivers a sensor from the sensor dispenser 10 to the meter 49. In addition, the alignment features can help orient and align a sensor mating mechanism 58 of the meter 49 so that the sensor mating mechanism 58 can receive a sensor 20 dispensed from sensor dispenser 10. Exemplary alignment features can include, markers (colors, arrows, etc.) indicating the orientation of the dispenser and/or surface contours that help guide the meter 49 into contact with the feeder mechanism 24.

Figure 9:
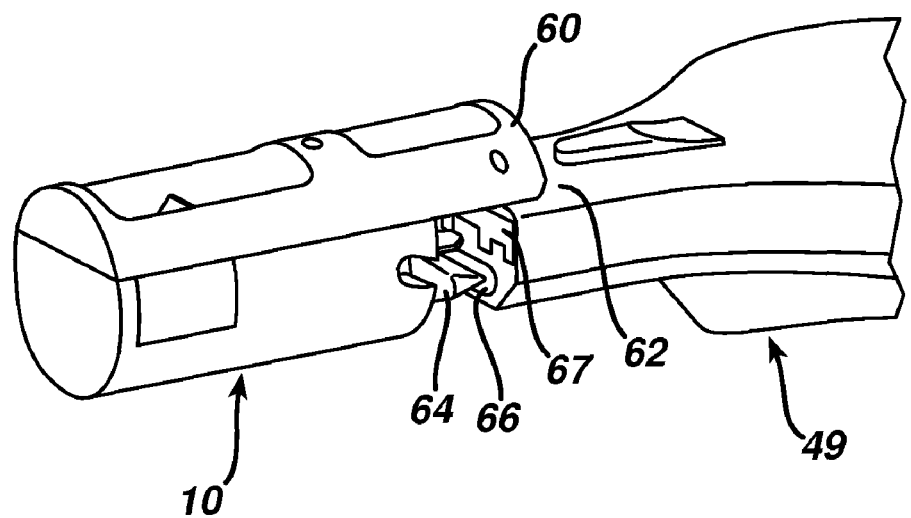
FIG. 9 is another view of the sensor dispenser and meter in a partially engaged configuration.

In order to facilitate coupling of the sensor dispenser 10 with a meter 49, the proximal surface of the dispenser 10 can be shaped and/or configured to match a corresponding shape on the meter 49. For example, FIG. 9 illustrates a sensor dispenser 10 wherein the proximal surface includes an extension portion 60 which extends proximally and corresponds to an upper surface 62 on the meter 49. In use, the upper surface 62 of the meter 49 can slide under the extension portion 60 and thereby guide the meter 49 into contact with the feeder mechanism 24. In another aspect, the sensor dispenser 10 can include a guide blade 64 that can be configured to mate within a recess 66 of the meter 49 when the dispenser and meter are properly aligned. The proximal surface of guide blade 64 can be tapered to facilitate insertion of the guide blade 64 into a recess of the meter 49. In use, these alignment features can be configured to prevent the sensor dispenser 10 and meter 49 from coupling unless the feeder mechanism 24 is properly aligned with the sensor mating mechanism 58.

As indicated above, various embodiments of a meter for receiving a sensor from the sensor dispenser 10 and performing a desired analysis are also provided herein. As will be apparent to those skilled in the art, the meter can be any type of meter capable of performing any of a wide range of analytical tests. For example, in an exemplary embodiment, the meter is an electrochemical meter configured to perform an electrochemical analysis. As indicated above, the meter can also be capable of receiving a sensor from the sensor dispenser when the meter is coupled to (or brought into proximity with) the dispenser. Once the sensor has been retained by the meter, a blood sample can be delivered to the sensor and the meter can perform the desired analysis. To facilitate the transfer of the sensor from the dispenser to the meter, the meter 49 can include a mating mechanism 58 configured for mating with sensors dispensed from the sensor dispenser 10 wherein the mating mechanism 58 can be configured to retain and/or lock a sensor within position during analysis. For example, the meter 49 can include a retention post 74 having a shape corresponding to at least a portion of the sensor 20. In use, when the meter 49 is brought into contact with a sensor 20 positioned within the feeder mechanism 24 (described above), the sensor can be directed into an opening 72 of the meter 49 and a retention post 74 can mate with sensor 20. In one embodiment, the meter 49 can mate with the sensor 20 at the same time that dispenser 10 is coupled with the sensor 20. For example, the retention post 74 can mate with a proximal portion of sensor 20 while the feeder mechanism 24 can mate with a distal portion of the sensor 20. Thus, bringing the meter 49 into contact with the feeder mechanism 24 which then releases the sensor 20 from the feeder mechanism 24 while the sensor 20 remains locked within meter 49. FIG. 11 shows the sensor 20 being positioned within the meter 49 while the retention post 74 retains the sensor 20 in position.

Figure 10:
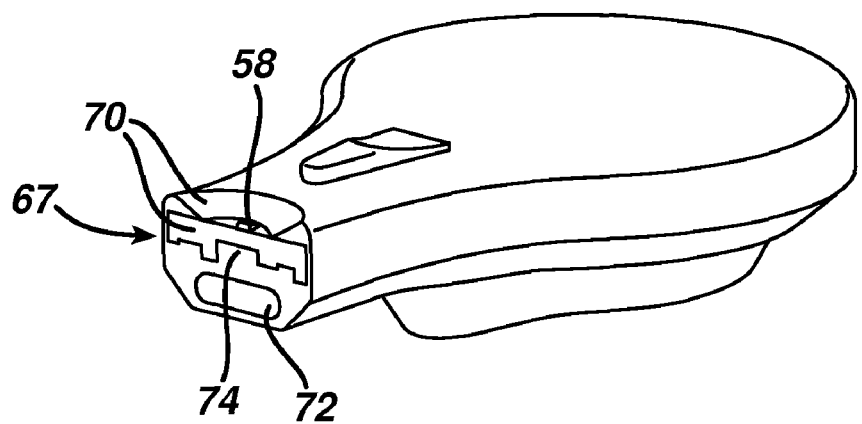

The meter 49 can also be configured to work with the feeder mechanism 24. For example, the distal surface of the meter 49 can include a locating surface 70 configured to contact the feeder mechanism 24. As shown in FIG. 10, the locating surface 70 can be tapered and/or recessed such that as the meter 49 is brought into contact with the sensor dispenser 10, the mating mechanism 58 can contact the sensor 20 prior to the feeder mechanism 24 releasing the sensor 20. Thus, as the meter 49 is coupled to the sensor dispenser 10, the locating surface 70 can contact the engaging member 40 thereby moving the engaging member 40 into the sensor dispensing configuration. Depending on the positioning of the engaging member 40 and the configuration of locating surface 70, the mating mechanism 58 can mate with the sensor 20 either prior to, at the same time as, or after the sensor dispenser 10 releases the sensor 20. In one embodiment, the meter 49 and the sensor dispenser 10 are configured such that feeder mechanism 24 and mating mechanism 58 can mate with sensor 20 at the same time.

The distal surface 67 of the meter 49 can also include various features which assist with directing the sensor 20 into the mating mechanism 58. For example, the distal surface 67 of the meter 49 can be tapered around an opening 72 to help guide the sensor 20 into the sensor mating mechanism 58. FIG. 10 shows a tapered lead-in surfaces on the distal surface of meter 49 that helps seat the sensor 20 within the sensor mating mechanism 58. Those skilled in the art will appreciate that the distal surface 67 of the meter 49 can also include various other features for assisting in directing the sensor 20 into the mating mechanism 58. All such embodiments are within the spirit and scope of the present disclosure.

The proximal portion of the meter 49 can also include a power source configured to electrically communicate with the sensor 20 and a processor for directing analysis, collecting data, and/or calculating a characteristic of an analyte (e.g., analyte concentration). In addition, the meter 49 can include a screen for interfacing with a user. One skilled in the art will appreciate that the meter 49 can be configured for analyzing samples using a variety of circuit configurations, user interfaces, and/or calculation schemes. Examples of suitable meter configurations are disclosed in U.S. Pat. No. 6,475,372 to Ohara et al. and U.S. Pat. No. 5,942,102 to Hodges, et al., the entirety of these references being incorporated herein by reference.

The sensor dispenser 10 and the meter 49 can also be configured to transmit and/or receive information between one another as a sensor 20 as the meter 49 and sensor dispenser 10 are brought into proximity with one another. An illustrative example of such communication is shown in FIGS. 13A-13D. In these embodiments, the sensor dispenser 10 can be associated with (e.g., coupled with, engaged to, etc.) some type of tag element 90 configured to store sensor-specific information. For example, the information can include a calibration code specific for each sensor container within the dispenser, a manufacture date, a lot or batch number, expiry date, or any other type of information specific to the sensor(s) disposed within the sensor dispenser 10. In other embodiments, the tag element 90 can store first information (e.g., a first calibration code) specific to a first plurality of sensors (e.g., sensors 1-5) and a second information (e.g., a second calibration code) specific to a second plurality of sensors (e.g. sensors 6-10) disposed within the container. Next, a meter 49 can be configured to read this information (e.g., via a reader element 92) from the tag element 90 of the sensor dispenser 10 each time the meter 49 retrieves a new sensor 20 from the sensor dispenser 10 thereby eliminating the need for a user to manually input the information into the meter 49. In use, the meter 49 can read the information from the sensor dispenser 10, retrieve a sensor 20 from the dispenser 10, perform an auto-calibration procedure which is at least partially dependent upon the sensor-specific information received from the tag element 90 of the sensor dispenser 10 (e.g., the information can be incorporated into a calibration algorithm performed within the meter 49), and finally the meter can perform an analysis on a blood sample which has been delivered to the sensor 20 within the meter 49.

As described above, the sensor dispenser 10 can include one or a plurality of sensors 20 configured for use with a meter 49. The sensors can be identical (e.g., be associated with the same calibration information) or the sensors can be distinct (e.g., associated with different calibration information). In an exemplary embodiment, a plurality of sensors 10 are disposed within the same sensor dispenser 10 because the sensors 20 are from the same manufacturing lot, share the same calibration requirements or manufacturing tolerances, or share some other feature in common. Thus, the tag element 90 of the sensor dispenser 10 can store one set of information which is related to each of the sensor(s) 20 within the sensor dispenser 10. This information can be any type or amount of information as desired by the user. For example, the information can include calibration data, date of manufacture, expiry date, strip lot number, control solution ranges, authentication code, inventory tracking and/or specific meter set up parameters. In an exemplary embodiment, the information can include a calibration code specific to each sensor(s). In use, upon reading the calibration code from the tag element 90, the meter 49 can incorporate the calibration code into an internal calibration algorithm, and subsequently performed the desired analysis.

Various procedures can be utilized to determine the sensor-specific information to be incorporated onto (e.g., written on) the tag element 90 of a specific sensor dispenser 10. In an exemplary embodiment, a set of substantially identical sensors 20 can be identified. Next, a plurality of un-calibrated test sensors 20 can be packaged within the sensor dispenser 10, and a sub-set of test sensors 20 can be tested individually so as to determine information specific to the sensors 20 of the sub-set. Once determined, the sensor-specific information can be programmed/written onto the tag element 90 in virtually any manner known by those skilled in the art. For example, the information can be programmed onto the tag element 90 via a contact-less manner using a writer device (e.g., a radiofrequency ("RF") writer). Additionally, the above-described process can be accomplished in large batches during the manufacturing procedure such as by passing the dispenser over an RF field that generates patterns suitable for programming the RF tag for example. Such a process would eliminate the labor and time involved in handling vials individually.

As will be appreciated by those skilled in the art, the tag element 90 can be any element configured to store the sensor-specific information and also configured to communicate (e.g., receive and/or transmit information) with the meter 49. In an exemplary embodiment, the tag element 90 is capable of wireless communication with the meter 49 thereby allowing for a wireless transfer of information from the tag element 90 to the meter 49. For example, the tag element 90 can be a radiofrequency ("RF") tag element 90 configured to communicate with the meter 49 via RF technology. As will be appreciated by those skilled in the art, various other such wireless and non-wireless technologies can be utilized to provide communication between the meter 49 and the sensor dispenser 10.

As indicated above, the meter 49 can also be configured to read and/or transmit information from the tag element 90. As will be appreciated by those skilled in the art, the meter 49 can be configured to perform such functions in various manners. For example, the meter 49 can be associated with some type of a reader element 92 configured to communicate with the tag element 90. Like the tag element 90, the reader element 92 can be any element configured to receive information from the tag element 90 thereby allowing the meter 49 to utilize the information in various calibration and/or analysis procedures. In an exemplary embodiment, the reader element 92 is configured to wirelessly communication with the tag element 90, for example, the reader element 92 can be a radiofrequency ("RF") reader element 92. Like above, the reader element 92 can communicate with the tag element 90 by either contact or non-contact methods. Contact methods remove the need for RF circuitry in the meter 49, thereby reducing the cost of such a system and eliminating problems such as spurious RF radiation.

Once the tag element 90 is positioned in the proximity of the reader element 92, communication can be triggered by either the tag element 90 or the reader element 92. For example, the reader element 92 can be activated by mechanical contacts, optical switches, or electrical switches (not shown) located inside the dispenser 10 receiving cavity of the meter 49, and can, for example, be included as part of a locating surface 70 or mating mechanism 58. Additionally, any of the alignment features previously described herein can assist in a successful transfer of information between the tag element 90 and the reader element 92. For example, the sensors which function to detect the presence of the dispenser 10 can be engaged with the meter 49 in order to receive a test sensor 20. The act of engagement between dispenser 10 and meter 49 and successful retrieval of a test sensor can trigger activation of the reader element 92 to poll for information from the tag element 90. In other embodiments, an energy source (e.g., a battery) capable of enabling or activating such communication can be disposed within or coupled to the sensor dispenser 10. Those skilled in the art will appreciate that various additional energy supplies can be utilize to power such communication.

Figure 13A:
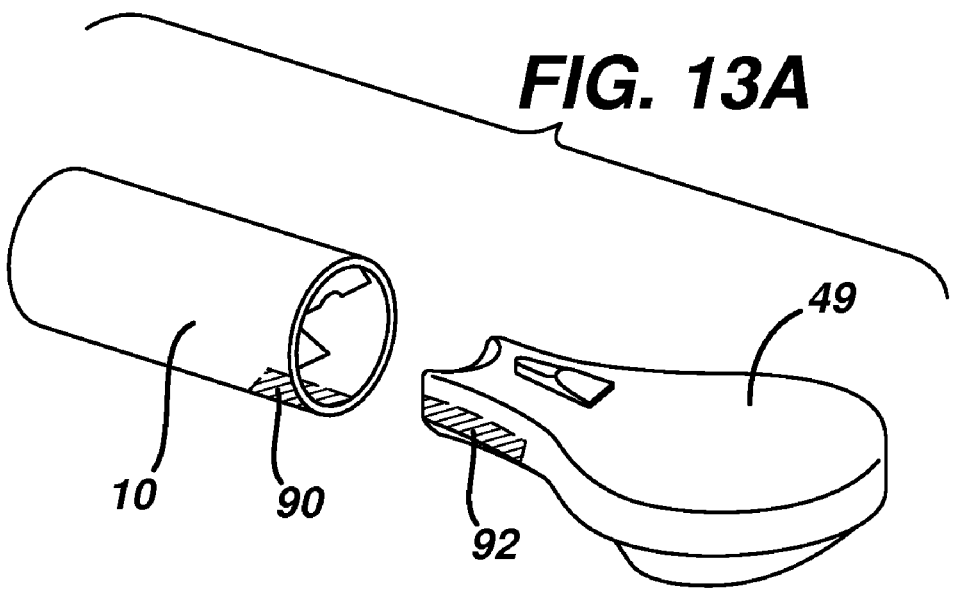
FIG. 13A is a perspective view of the sensor dispenser and meter of FIG. 11A including a tag element associated with the dispenser and a reader element associated with the meter.
Figure 13B:
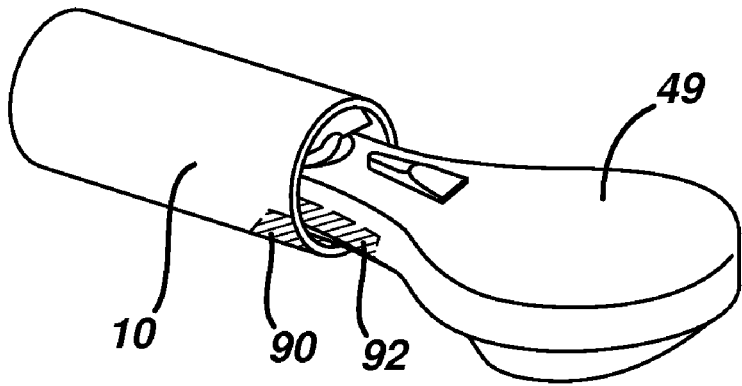
FIG. 13B is a perspective view of the system of FIG. 13A showing the meter coupled with the dispenser thereby enabling communication between the tag element and the reader element.
Figure 13C:
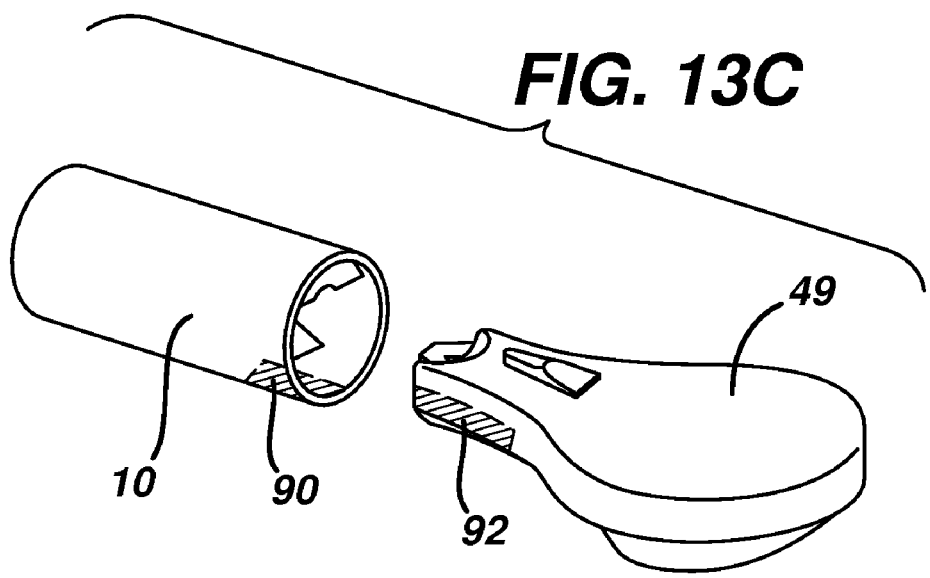
FIG. 13C is a perspective view of the dispenser being decoupled from the meter.
Figure 13D:
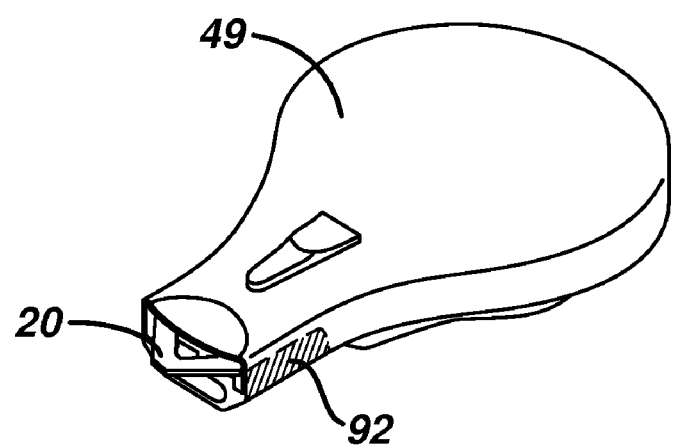
FIG. 13D is a perspective view of the meter retaining a test sensor retrieved from the dispenser.

As indicated above, FIGS. 13A-13D illustrate an exemplary embodiment of the transfer of information between the tag element and the reader element. More specifically, FIG. 13A shows a sensor dispenser 10 having an RF tag 90 and a meter 49 having an RF reader 92. As shown, the RF tag 90 and the RF reader 92 are positioned at corresponding locations such that the RF tag 90 and the RF reader 92 can communicate when brought into proximity with one another. As will be appreciated by those skilled in the art, the tag element 90 and the reader 92 can be positioned at any other location relative to one another as long as the two elements 90, 92 can communicate with one another (as shown in FIG. 13B). Preferably, the transfer of information can occur when the meter 49 is coupled to the sensor dispenser 10. Next, as shown in FIG. 13C, the dispenser 10 can be decoupled (or merely withdrawn) from the meter 49 thereby allowing the meter 49 to retain a sensor 20 therein (see FIG. 13D). At this stage, the meter 49 is calibrated (or other/additional steps performed with the information) relative to the sensor 20 retained therein and thereby capable of performing an accurate analysis.

Various embodiments of a method of using a sensor dispenser 10 to dispense a sensor 20 are also provided herein. In one such embodiment, the method includes using a meter 49 to activate a sensor dispenser 24 and thereby dispensing a sensor 20 from the sensor dispenser 10 to the meter 49. For example, FIGS. 11A through 11D illustrate the operation of a sensor dispenser 10 in dispensing a sensor 20 to a meter 49. More specifically, prior to delivery of a sensor, a user can initially prepare the dispenser 10 for operation by opening access to the sensor feeding mechanism 24. For example, as indicated above, the body 12 of the dispenser can include a resealable access port at a proximal end 14, such as an air tight cap shown in FIGS. 2A and 2B. In use, opening the proximal end of dispenser 10 can provide access to the proximal surface of sensor feeding mechanism 24.

Figure 11A:
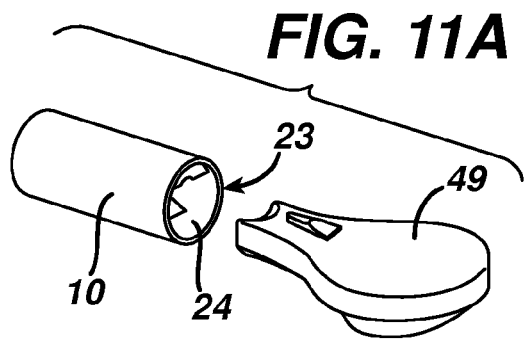
FIG. 11A is a perspective view of the sensor dispenser prior to coupling of the sensor dispenser with the meter.
Figure 11B:
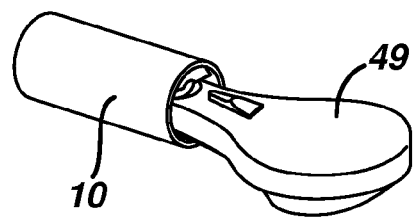
FIG. 11B is a perspective view of the meter being coupled with the sensor dispenser.
Figure 11C:
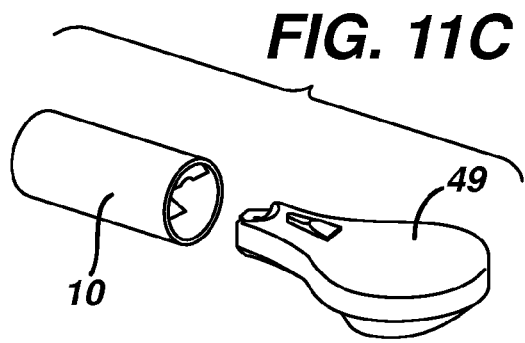
FIG. 11C is a perspective view of the sensor dispenser and the meter with a dispensed sensor.

Once such access has been provided, a user can align the dispenser 10 with the meter 49 and bring the sensor feeding mechanism 24 into contact with the sensor mating mechanism 58 thereby allowing for delivery of an individual sensor from a sensor dispenser 10 to the meter 49. For example, FIG. 11A shows the sensor dispenser 10 and the meter 49 being properly oriented and ready to engage one another. As the dispenser 10 and the meter 49 are brought together, the alignment features discussed above can assist with fine tuning of the alignment of the feeder mechanism 24 and the mating mechanism 58. FIG. 11B illustrates the meter 49 engaged with the sensor dispenser 10. In other embodiment, a sensor can be transferred to the meter without the meter being mated to the dispenser.

Figure 11D:
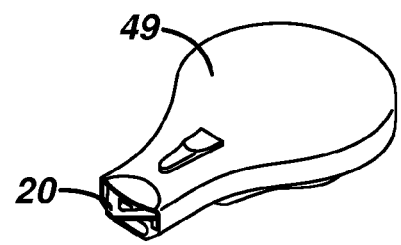
FIG. 11D is a perspective view of the meter having a sensor retained therein.

Once the sensor 20 is retained within the meter 49, a sample of physiological fluid (e.g., blood) can be administered to the sensor and testing can proceed. As will be apparent to those skilled in the art, the meter and/or sensor can be selected to provide virtually any type of desired analysis. In an exemplary embodiment, the sensor 20 and the meter 49 can be used to determine the concentration of glucose in whole blood. Thus, the user can deliver a sample (e.g., a whole blood sample) into a reaction chamber within the sensor, and the sample can react with a reagent(s) and electrodes positioned therein. For example, the meter can create an electrical potential across the electrodes and collect any data (e.g., time and current data) resulting therefrom. Based on the collected data the meter can provide the user with information about an analyte within the sample (e.g., glucose concentration). For illustrative purposes, FIG. 11D shows a sensor 20 ready to receive a sample.

Figure 12A:
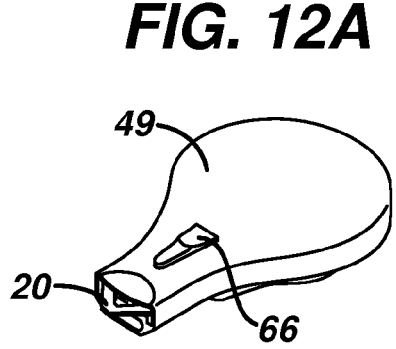
FIG. 12A is a perspective view of the meter with a sensor retainer therein.
Figure 12B:
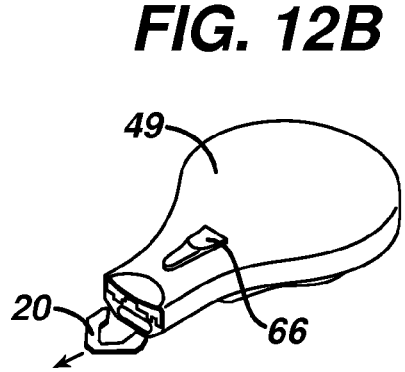
FIG. 12B is a perspective view of the sensor and meter of FIG. 12A with the sensor being ejected from the meter.

In an exemplary embodiment, the sensor 20 is generally intended for a single use and can be disposed of after analysis. For example, as shown in FIGS. 12A and 12B, after completion of a test, the user can eject the spent sensor. In one embodiment, the sensor 20 can be ejected from meter 49 by depressing and/or advancing an ejection button 66. The testing procedure can be repeated, as desired, by feeding another sensor to meter 49 from sensor dispenser 10. Those skilled in the art will appreciate that various reusable sensors are within the spirit and scope of the present disclosure.

As indicated above, any of a wide range of sensors are included within the spirit and scope of the present disclosure. For example, the sensor can be an electrochemical sensor having spaced apart electrodes that define a reaction chamber. The sensor can further include electrical contacts positioned in various locations (e.g., positioned on the surface of the sensor) which are in electrical contact with the electrodes. These contacts allow the meter to electrically communicate with the electrodes positioned within the reaction chamber. FIGS. 3 and 4 illustrate one exemplary embodiment of a generally "V" shaped sensor that can be used with dispenser 10 and that includes a longitudinal reaction chamber 80 with laterally spaced electrical contacts 82. In one aspect, the reaction chamber 80 can be positioned towards a distal end of the sensor and electrical contacts 82 can be positioned toward a proximal end of the sensor. In use, the sensor can be dispensed proximal end first, thereby allowing the meter to receive the electrical contacts 82.

Figure 14:
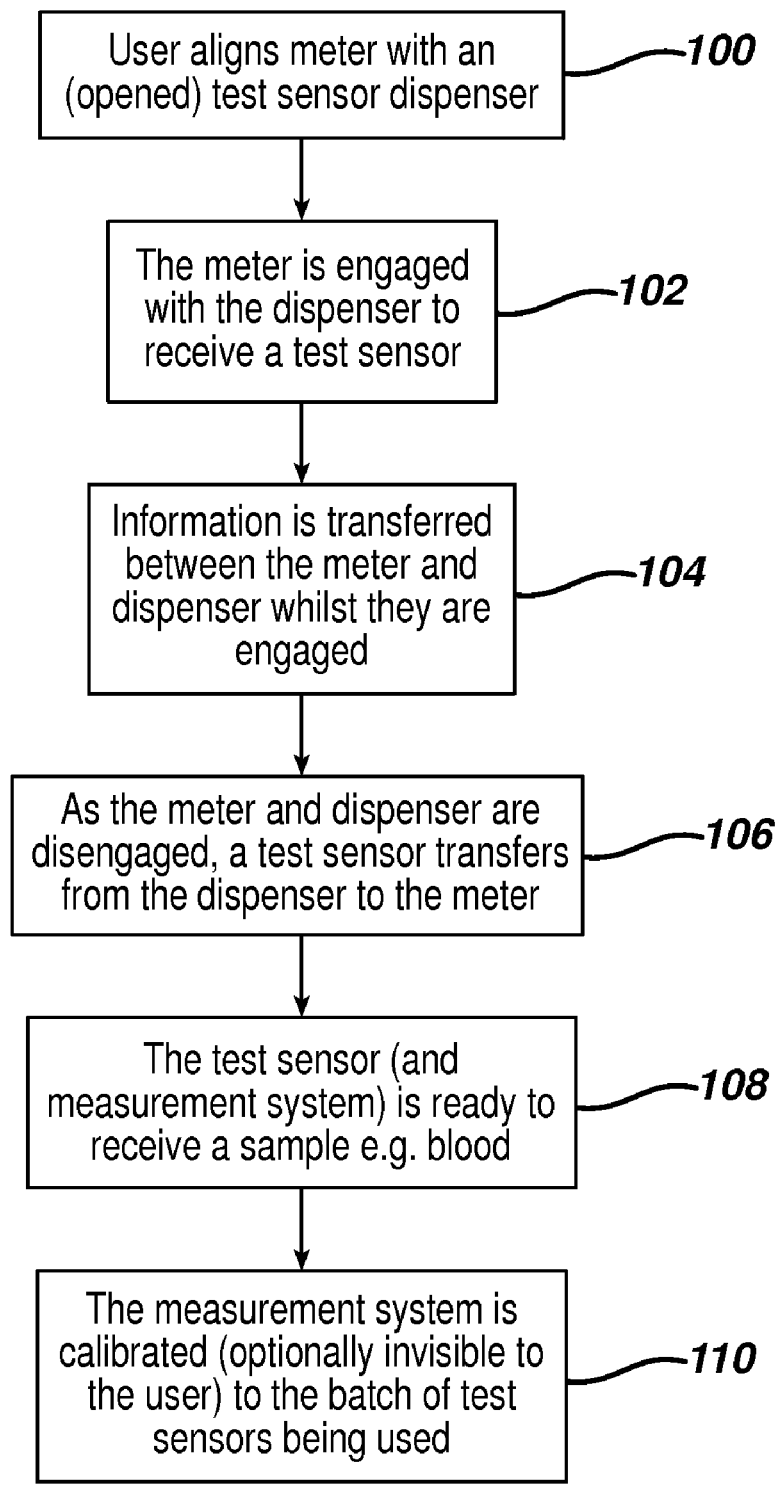
FIG. 14 is a flow diagram of steps utilized in an embodiment of the method.

The sensor 20 can also include features that assist with dispensing. For example, an embodiment of the sensor 20 is shown in FIGS. 3 and 4 which includes an open region 26 configured to receive at least a portion of sensor dispenser 10. As described above, the dispenser 10 and the meter 49 can mate with the surface features, such as the open region 26, for holding and/or dispensing the sensor. One skilled in the art will appreciate that the sensor 20 can include a variety of other features for mating with the dispenser 10, such as notches in the side of the sensor, apertures through the sensor, recesses or protrusions on the sensor, and various combinations thereof. One skilled in the art will appreciate that sensor 20 can include the variety of electrochemical sensors capable of being dispensed from a dispenser. Exemplary sensors are described in U.S. patent application Ser. No. 11/138,080, filed May 25, 2005, entitled "Method and Apparatus for Electrochemical Analysis," this application being incorporate Additionally, various embodiments of a method of auto-calibrating a meter are also provided herein. FIG. 14 provides a flow-chart illustrating various steps of an exemplary embodiment of the method wherein the sensor dispenser 10 can communicate with the meter 49 thereby allowing for the meter 49 to perform an auto-calibration step as a sensor 20 is brought into proximity with the meter 49. As shown, initially, the meter 49 can be aligned with the dispenser 10 (which may or may not have to be opened), step 100. Next, the meter 49 can be engaged with (or brought into proximity to) the dispenser 10 in order to receive a test sensor, step 102. Next, information pertinent to the test sensor being moved from the dispenser to the meter can be transferred from the dispenser 10 to the meter 49, step 104. Next, as the meter and dispenser are disengaged (or withdrawn from one another), a test sensor can be transferred from the dispenser 10 to the meter, step 106, leaving the meter 49 ready to receive a biological sample (e.g. blood), step 108. The meter is thereby calibrated to the particular test sensor being used. Such calibration can proceed through a process that may be visible i.e. via messages on the display of the meter, or optionally, invisible to the user, step 110.

One skilled in the art will appreciate further features and advantages of the presently disclosed system and method based on the above-described embodiments. Accordingly, the present disclosure is not to be limited by what has been particularly shown and described, except as indicated by the appended claims. All publications and references cited herein are hereby expressly incorporated herein by reference in their entirety.

What is claimed is:

1. A method of auto-calibrating a meter, comprising:
   providing a set of sensors wherein different sub-sets of the sensors are associated with different calibration information;
   determining a set of calibration information applicable to each sub-set of the set of sensors, wherein said determination includes individually testing each of the sub-set of sensors in order to determine their respective calibration;
   storing onto a tag element each of the different sets of calibration information as well as sensor type information;
   associating the tag element with a sensor dispenser; and
   disposing a plurality of sensors from two or more of the sub-sets of sensors within a sensor dispenser, the sensor dispenser configured to deliver one sensor to a meter upon demand; and
   placing the tag element into communication with a reader element associated with the meter, the reader element configured to receive information from the tag element and to allow for the information to be utilized in a meter auto-calibration procedure and a sensor type identification procedure.

2. The method of claim 1, wherein the tag element is an RF tag.

3. The method of claim 2, wherein the receiver element is an RF receiver.

4. The method of claim 1, further comprising:
following the placing step, activating the receiver element thereby allowing the receiver element to communicate with the tag element.

5. The method of claim 1, further comprising:
following the placing step, activating the tag element thereby allowing the receiver element to communicate with the tag element.

6. The method of claim 1, wherein the tag element is further configured to receive information from the reader element, and the reader element is further configured to store information capable of being read by the tag element.

7. The method of claim 1, wherein the meter is configured to determine a glucose concentration of a blood sample.

8. The method of claim 1, wherein the sensor dispenser is substantially cylindrical with the tag element coupled to a distal end of the dispenser, the distal end of the dispenser configured to releasably engage the meter such that the reader element coupled to the meter is in communication with the tag element when the meter is engaged to the sensor dispenser.

9. A method of measuring an analyte concentration in a blood sample, comprising:
utilizing a set of sensors wherein different sub-sets of the sensors are associated with different calibration information;
utilizing a sensor dispenser having a plurality of sensors from two or more of the sub-sets of sensors disposed therein, the sensor dispenser configured to deliver one sensor to a meter upon demand, the sensor dispenser associated with a tag element that stores a set of calibration information applicable to each sub-set of sensors as well as sensor type information;
positioning a meter into communication with the sensor dispenser such that a reader element associated with the meter can receive information from the tag element thereby allowing the meter to perform an auto-calibration step and a sensor type identification step which are at least partially dependent upon the information;
transferring a sensor from the sensor dispenser to the meter;
removing the meter from communication with the sensor dispenser;
applying a biological sample to the sensor; and performing a desired analysis of the sample.

10. The method of claim 9, wherein the desired analysis includes identification of an analyte within a blood sample.

11. The method of claim 10, wherein the analyte is glucose.

12. The method of claim 9, wherein the tag element is an RF tag.

13. The method of claim 12, wherein the receiver element is an RF receiver.

14. A system for auto-calibration of a meter, comprising:
a set of sensors wherein different sub-sets of the sensors are associated with different calibration information;
a sensor dispenser configured to retain a plurality of sensors from two or more of the sub-sets of sensors, the sensor dispenser configured to deliver one sensor to a meter upon demand, the sensor dispenser associated with a tag element that stores a set of calibration information applicable to each sub-set of sensors as well as sensor type information; and
a meter configured to receive a sensor from the sensor dispenser, the meter further associated with a reader element configured to communicate with the tag element as the reader element and tag element are brought into communication thereby allowing the meter to perform an auto-calibration step and a sensor type identification step which are at least partially dependent upon the information received from the tag element.

15. The system of claim 14, wherein the tag element is an RF tag.

16. The system of claim 15, wherein the reader element is an RF reader element.

17. The system of claim 14, wherein the meter is configured to determine a glucose concentration present in a blood sample.

18. The system of claim 14, wherein the meter further includes a counter element configured to determine a number of sensors received from a particular sensor dispenser.

19. A system for auto-calibration of a meter, comprising:
a set of sensors wherein different sub-sets of the sensors are associated with different calibration information
a sensor dispenser configured to house a plurality of sensors from two or more of the sub-sets of sensors, the sensor dispenser configured to deliver one sensor to a meter upon demand; and
a tag element associated with the sensor dispenser, the tag element storing a set of calibration information applicable to each sub-set of sensors as well as sensor type information, wherein said information is determined by identifying a sub-set of sensors related to the plurality of sensors, and individually testing each of the sub-set of sensors in order to determine the set of information from the sub-set of sensors, the tag element further configured to communicate the information to a meter.

20. The system of claim 19, wherein the tag element can wirelessly communicate the information to a meter.

21. The system of claim 20, wherein the tag element is a RF tag element configured to communicate the information to a meter via wireless RF technology.

22. The system of claim 21, wherein the meter is configured to perform an auto-calibration step which is at least partially dependent upon the information received from the tag element.

23. A system for auto-calibration of a meter, comprising:
a set of sensors wherein different sub-sets of the sensors are associated with different calibration information
a sensor dispenser configured to house a plurality of sensors from two or more of the sub-sets of sensors, the sensor dispenser configured to deliver one sensor to a meter upon demand;
a tag element associated with the sensor dispenser, the tag element storing the different sets of information as well as sensor type information, wherein said information is determined by identifying a sub-set of sensors related to the plurality of sensors, and individually testing each of the sub-set of sensors in order to determine the set of sensor-specific information from the sub-set of sensors;
a meter configured to receive a sensor from the sensor dispenser; and
a reader element associated with the meter, the reader element configured to receive an amount of the sensor-specific information from the sensor dispenser.

* * * * *